United States Patent [19]

Andrianov et al.

[11] Patent Number: 5,500,161
[45] Date of Patent: Mar. 19, 1996

[54] METHOD FOR MAKING HYDROPHOBIC POLYMERIC MICROPARTICLES

[75] Inventors: Alexander K. Andrianov, Belmont; Robert S. Langer, Newton, both of Mass.

[73] Assignee: Massachusetts Institute of Technology and Virus Research Institute, Cambridge, Mass.

[21] Appl. No.: 124,816

[22] Filed: Sep. 21, 1993

[51] Int. Cl.⁶ .......................................... B29B 9/00
[52] U.S. Cl. ................................ 264/8; 264/9; 264/11; 264/12; 264/14
[58] Field of Search ............................. 264/5–14

[56] References Cited

U.S. PATENT DOCUMENTS

| | | | |
|---|---|---|---|
| 3,773,919 | 11/1973 | Boswell et al. | |
| 4,016,098 | 4/1977 | Saeki et al. | |
| 4,021,364 | 5/1977 | Speiser et al. | |
| 4,063,017 | 12/1977 | Tsao | 536/57 |
| 4,091,058 | 5/1978 | Sander | 264/11 |
| 4,352,883 | 10/1982 | Lim | |
| 4,440,921 | 4/1984 | Allcock et al. | |
| 4,469,648 | 9/1984 | Ferraris | 264/9 |
| 4,495,174 | 1/1985 | Allcock et al. | |
| 4,663,447 | 5/1987 | Yamazaki | 264/13 |
| 4,765,973 | 8/1988 | Heller | |
| 4,880,622 | 11/1989 | Allcock et al. | |
| 4,908,233 | 3/1990 | Takizawa et al. | |
| 4,933,105 | 6/1990 | Fong | 264/12 |
| 4,946,938 | 8/1990 | Magill et al. | |
| 5,019,400 | 5/1991 | Gombotz | 424/497 |
| 5,047,180 | 9/1991 | Steiner | 264/12 |
| 5,063,109 | 11/1991 | Bieniarz | 428/378 |
| 5,089,272 | 2/1992 | Shioya et al. | |
| 5,120,349 | 6/1992 | Stewart et al. | |
| 5,126,381 | 6/1992 | Liscomb | 264/12 |
| 5,132,117 | 7/1992 | Speaker et al. | |
| 5,149,543 | 9/1992 | Cohen et al. | |
| 5,277,979 | 1/1994 | Kiebania, Jr. et al. | |
| 5,308,701 | 5/1994 | Cohen et al. | |
| 5,310,867 | 5/1994 | Besecke | 528/502 |
| 5,334,394 | 8/1994 | Kossovsky | 424/494 |

FOREIGN PATENT DOCUMENTS

| | | |
|---|---|---|
| 377477 | 3/1993 | European Pat. Off. |
| 60-34731 | 2/1985 | Japan |

OTHER PUBLICATIONS

Merck Index, 11th ed., 1989, p. 1401.

Allcock, H. R. et al., "Amphiphilic polyphosphazenes as membrane materials: influence of side group on radiation cross–linking", *Biomaterials*, 9:500–508 (1988).

Allcock, H. R. et al., "An Ionically Cross–Linkable Polyphosphazene: Poly[bis(carboxylatophenoxy)phosphazene] and its Hydrogels and Membranes", *Macromolecules*, 22:75–79 (1989).

Allcock, H. R. et al., "Convalent Linkage of Proteins to Surface–Modified Poly(organophosphazenes): Immobilization of Glucose–6–Phosphate Dehydrogenase and Trypsi", *Macromolecules*, 19:1502–1508 (1986).

Allcock, H. R. et al., "Glyceryl Polyphosphazenes: Synthesis, Properties, and Hydrolysis", *Macromolecules*, 21(7):1980–1985 (1988).

(List continued on next page.)

*Primary Examiner*—Chester T. Barry
*Attorney, Agent, or Firm*—Arnall Golden & Gregory

[57] ABSTRACT

A method for the preparation of microparticles, and the product thereof, that includes dispersing a substantially water insoluble non-ionic or ionic polymer in an aqueous solution in which the substance to be delivered is also dissolved, dispersed or suspended, and then coagulating the polymer together with the substance by impact forces to form a microparticle. In an alternative embodiment, the microparticle is formed by coagulation of an aqueous polymeric dispersion through the use of electrolytes, pH changes, organic solvents in low concentrations (the minimal amount necessary to break up the dispersion), or temperature changes to form polymer matrices encapsulating biological materials.

26 Claims, 1 Drawing Sheet

FITC-BSA RELEASE
EUDRAGIT NE 30D MICROSPHERES

Loading - 4.27% (dry microsphere weight)
Efficiency of encapsulation - 64.7%

OTHER PUBLICATIONS

Allcock, H. R. et al., "Hydrolysis Pathways for Aminophosphazenes", *Inorg. Chem.,* 21(1):515–521 (1982).

Allcock, H. R. et al., "Phosphonitrilic Compounds, XV. High Molecular Weight Poly[bis(amino)phosphazenes] and Mixed–Substituent Poly(aminophosphazenes)", *Inorganic Chemistry,* 11(7):2584–2590 (1972).

Allcock, H. R. et al., "Synthesis of Poly[(amino acid alkyl ester)phosphazenes]", *Macromolecules,* 10(4):824–830 (1977).

Allcock, H. R. et al., "Synthesis of Sugar–Substituted Cycli and Polymeric Phosphazenes and Their Oxidation, Reduction, and Acetylation Reactions", *Macromolecules,* 16(5):715–719 (1983).

Allcock, H. R. et al., *J. Inorg. Chem.,* 5:1706 (1966)*.

Bodmeier and Wang, "Microencapsulation of Drugs with Aqueous Colloidal Polymer Dispersions," *Journal of Pharmaceutical Sciences,* 82(2):191–194 (1993).

Grolleman et al., *J. Controlled Release,* 3:143 (1986)*.

Lehmann, "Chemistry and Application Properties of Polymethacrylate Coating Systems," *Drugs and The Pharmaceutical Sciences, Aqueous Polymeric Coatings for Pharmaceutical Dosage Forms Ed. J. W. McGinity, Marcel Dekker, Inc., New York and Basel, 36:153–245 (1989).*

Mosmann, T. J., *Immunol. Methods,* 65:55 (1983)*.

Sanders, L. M. et al., "Controlled Release of a Luteinizing Hormone–Releasing Hormone Analogue from Poly(d.l–lactide–co–glycolide) Microspheres", *Journal of Pharmaceutical Sciences,* 73(9):1294–1297 (1984).

Selgen, P. O., "In Methods of Cell Biology", ed. Prescott, E., New York:Academic Press, p. 13 (1976)*.

Szoka, et al., *Proc. Natl. Acad. Sci.* USA, 75:4194 (1978)*.

METHOD FOR MAKING HYDROPHOBIC POLYMERIC MICROPARTICLES

BACKGROUND OF THE INVENTION

This invention is a method for the preparation of hydrophobic polymeric microparticles which are useful for protein drug delivery, and the microparticles prepared thereby.

Microparticles prepared from synthetic polymers are currently a popular means to deliver drugs or other substances in a controlled fashion because of the chemist's ability to tailor the polymer properties to satisfy particular needs, such as degradability, swelling, permeability, temperature and pH sensitivity. Synthetic polymers must be selected that are hydrophobic so that they retain their integrity for a suitable period of time when placed in an aqueous environment, such as the body, and stable enough to be stored for an extended period before use.

A number of polymers have been used as a matrix material for delivery devices, including polyanhydrides, polyesters, polyamides, polyurethanes, polyorthoesters, polyacrylonitriles, and polyphosphazenes. Examples of synthetic polymers used for encapsulation of bioactive substances are described in European Patent Application No. 377 477.

Hydrophobic polymeric delivery devices are currently prepared in a variety of ways. A number of processes involve the use of heat. One example is the melt fabrication technique, that includes the steps of melting a polymer, mixing the melted polymer with the substance to be delivered, and then solidifying the loaded polymer by cooling. Melt fabrication processes can only be used with polymers that have a melting point that is below the temperature at which the substance to be delivered and polymer degrade or become reactive. Microparticle fabrication techniques that involve heat are not suitable for the loading of sensitive biological materials, such as proteins, bacteria, cells, including human cells, and liposomes, which are destroyed or inactivated under these conditions.

Microencapsulation has also been accomplished by spray-drying, wherein aqueous latexes of polymers or organic solutions of polymers are sprayed in a stream of hot air, and dried simultaneously. The water or other solvent is eliminated from the latex on exposure to the hot air, that is typically at a temperature of up to 140° C. This technique cannot be used with soft polymer latexes which have a glass transition temperature near room temperature.

Alternatively, the device can be prepared by solvent casting (referred to as the solution evaporation or phase separation technique), wherein the polymer is dissolved in a solvent, and the substance to be delivered dissolved or dispersed in the polymer solution. The solvent is then evaporated or otherwise separated, leaving the substance in the polymeric matrix. For example, the '477 European Patent Application discloses a process for the preparation of microcapsules wherein the bioactive substance to be delivered is initially dispersed in an organic solution of polymer, and a second "hardening" organic liquid added to force phase separation of the polymer with encapsulated bioactive substance from the solution. The microcapsules are then collected, washed and dried.

Solvent casting requires that the polymer be soluble in organic solvents, and is limited to the preparation of microparticles loaded with materials that are not sensitive to organic solvents. Organic solvents often adversely affect biologically active materials. For example, sensitive proteins, including antigens and enzymes, can be denatured by organic solvents. Beneficial bacteria, including genetically engineered bacteria, and cells, including human cells, can be killed by organic solvents, and liposomal structures can be broken down by organic solvents.

Polyelectrolytes can be used for the encapsulation of biologically-labile materials without the use of heat or organic solvents. U.S. Pat. No. 5,149,543 describes a process wherein water-soluble polyelectrolytes are crosslinked with multivalent ions of opposite charge to form a gel capable of encapsulating biological material. This method is limited to polymers containing ionic groups and requires a microcapsule stabilization stage due to the sensitivity of ionotropic gels to ionic strength and pH changes.

In light of the strong need to deliver sensitive biological materials, such as proteins, bacteria, cells, including human cells, and liposomes, in a controlled fashion to a patient, it would be desirable to have a process for the encapsulation of these materials that does not require harsh conditions that can adversely affect the material, such as elevated temperature, or the use of organic solvents. It would also be desirable to have a process for the encapsulation of sensitive biological materials that does not require a stabilization step.

It is therefore an object of the present invention to provide a process for the preparation of microparticles that does not require the use of elevated temperatures or organic solvents.

It is another object of the present invention to provide a process for the preparation of microparticles of sensitive biological materials that does not require a stabilization step.

It is another object to provide microparticles with incorporated substances that are not prepared under harsh conditions that adversely affect the substance.

SUMMARY OF THE INVENTION

A method for the preparation of microparticles containing a substance to be delivered, and the product thereof, are disclosed. The method can be used to encapsulate biologically active materials, including labile materials such as proteins, liposomes, and procaryotic and eucaryotic cells. The method includes dispersing a substantially water insoluble non-ionic or ionic polymer in an aqueous solution in which the substance to be delivered is also dissolved, dispersed or suspended, and then coagulating the polymer together with the substance by impact forces to form a microparticle.

In an alternative embodiment, the microparticle is formed by coagulation of an aqueous polymeric dispersion through the use of electrolytes, pH changes, organic solvents in low concentrations (the minimal amount necessary to break up the dispersion), or temperature changes to form polymer matrices encapsulating biological materials.

The shape and size of microspheres depend on the polymeric dispersion concentration, polymer extrusion rate, air pressure and configuration of nozzle.

A preferred means to coagulate the polymer with the substance to be delivered is by shear coagulation, wherein the aqueous polymeric dispersion is forced through an air-atomization nozzle, pneumatic nozzle, or microfluidizer. Coagulation can also be induced by steep shearing gradients in high-speed stirrers or colloid mills. As an example, a 7% dispersion of poly(lactic acid) mixed with 20% Pluronic™ (a block copolymer of polyethylene oxide and polypropylene oxide, supplied by BASF Corporation) with a particle size smaller 10–15 μm was coagulated into particles of irregular shape with a size larger than 30–50 μm using a microfluidizer.

In one embodiment, microparticles can be produced using the mild technique of simultaneous coagulation and spraying of a mixture of an aqueous polymer dispersion and a solution of biological material to be encapsulated into deionized water. Microparticles prepared in this manner can be loaded with sensitive biological materials that are not significantly denatured, degraded, killed, or otherwise inactivated.

Microparticles can be prepared from nonbiodegradable polymers such as acrylates or methacrylates, or from biodegradable polymers. In a preferred embodiment, the microparticle is fabricated from EUDRAGIT NE 30 D (Rohm Pharma GmbH, Weigerstadt, a copolymer of ethylacrylate and methylmethacrylate in a molar ratio of 2:1 of the two monomers, respectively, a mean molecular weight of 800,000 Da, which is dispersed in water to form a 30% aqueous dispersion with mean particle size 250 nm). The copolymer is not rapidly degraded in vivo. The copolymer swells in water. Biologically active molecules pass through the polymer substantially by diffusion when the system is exposed to an aqueous environment. The permeability of the polymer matrix can be reduced by addition of hydrophobic substances or can be increased by hydrophilic substances.

Biodegradable polymers that can be used as the matrix material include those that degrade enzymatically and those that degrade hydrolytically. While the process described herein is a water-based process, hydrolytically unstable polymers can be used in the process as long as they do not degrade to an unacceptable extent during the short time that they are in the aqueous solution during fabrication.

DETAILED DESCRIPTION OF THE INVENTION

Figure 1:
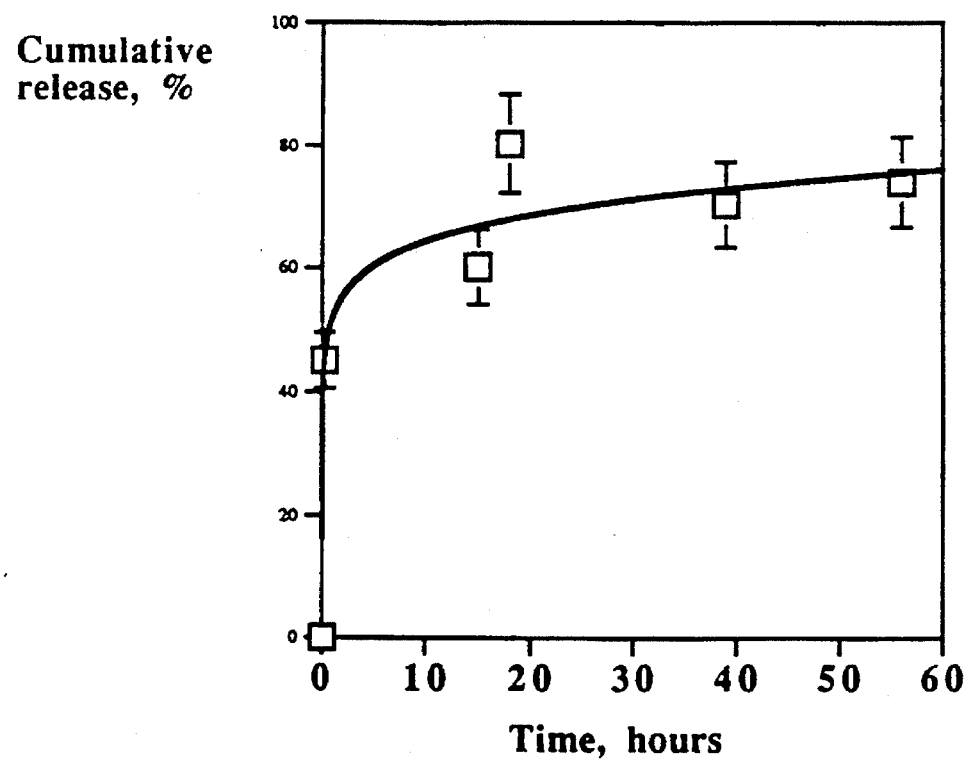
FIG. 1 is a graph of the percent cumulative release over time (hours) of fluorescein-labeled bovine serum albumin (FITC-BSA) from microspheres of poly(ethyl acrylate-co-methyl methacrylate) (monomer ratio 2:1, respectively, mean molecular weight 800,000 Da). The microspheres were loaded with 4.27% FITC-BSA with an efficiency of encapsulation of 64.7%.

A method for the preparation of microparticles loaded with a substance, and in particular, a biologically active material, and the product thereof, are disclosed. The process represents a significant advance in the art of the preparation of pharmaceutical delivery devices, in that it avoids the use of organic solvents, can be carried out without heat, if desired, is highly reproducible and requires few processing steps.

In a preferred embodiment, the process is carried out at ambient temperature or below. The process can alternatively be carried out at an elevated temperature below the boiling temperature of water, as desired, if the substrate is not temperature sensitive. As the temperature is increased, in general, the size of the microparticle increases.

Microparticles can be prepared using this process that have a wide range of shapes and sizes. As used herein, the term microparticle refers to a solid particle typically ranging in size between approximately 1 and 1000 microns. Microparticles between approximately one and ten microns are often used for certain biological applications, such as for the oral administration of vaccines, and a size of less than 8 μm used for diagnostic imaging microcapsules for lungs. Spherical particles are preferred for many biological applications, however, nonspherical particles can be used in appropriate cases.

Different coagulation techniques can produce microparticles of differing shapes. For example, it has been observed that coagulation by air atomization usually provides spherical microparticles, whereas microfluidizers typically produce irregularly shaped particles.

Any hydrophobic polymer can be used in the preparation of the microparticle that provides the desired product using the procedure described herein, including biodegradable and nonbiodegradable polymers. Likewise, any desired substance can be encapsulated in the microparticle using this process, including biologically-labile materials. Nonlimiting examples of polymers for encapsulation and substances that can be delivered are described in detail in Sections I and II, respectively. The process for producing hydrophobic polymeric microparticles is described in detail in Section III. Given the description of the process set out below, one of ordinary skill in the art will be able to prepare a wide variety of microparticles for diverse applications, all of which are intended to fall within the scope of this invention.

I. Selection of Polymers for Preparation of Microparticle

A wide variety of polymers can be used to form the microparticles described herein. A polymer should be selected that: (1) is substantially insoluble, and preferably, soluble only to an extent of approximately 1% or less by weight, in the aqueous solution of use for the dispersion, such as water, a buffered salt solution, or aqueous acid, base or alcohol solution; and (ii) can form an aqueous dispersion (preferably 1–45% w/w polymer in aqueous solution) in the presence or absence of an agent modifying the surface properties of the polymer. For example, Eudragit S100 polymers (copolymer of methacrylic acid and methylmethacrylate in a ratio of 1:2, mean MW 135,000 Da, Rohm Pharma GmbH, Weigerstadt) are insoluble at a pH below 7, Eudragit L100 polymers (copolymer of methacrylic acid and methylmethacrylate in a ratio of 1:1, mean MW of 135,000 Da) are insoluble at a pH below 6, and Eudragit L30D polymers (copolymer of methacrylic acid and ethylacrylate, in a ratio of 1:1, molecular weight of 250,000 Da) are insoluble below pH 5.5. Water-swellable polymers can also be used to prepare the microcapsule. In addition, mixtures of polymers and polymer blends can be used to fabricate the microparticle.

Examples of polymers that fall within these categories are partially or completed esterified polymers or copolymers of acrylic or methacrylic acid, polyphosphazenes, polycarbonates, polylactic acid, polyglycolic acid, copolymers of lactic acid or glycolic acid, for example, polymers or copolymers of lactic acid or glycolic acid with alkylene glycols, including but not limited to ethylene glycol and propylene glycol, polyhydroxybutyric acid, polyorthoesters, polyanhydrides, polysiloxanes, polycaprolactone, or copolymers prepared from the monomers of these polymers. Water-swollen copolymers of monomers of the above polymers with monomers of hydrophilic polymers such as polyvinylpyrrolidone, polyvinylalcohol, polyhydroxyethylmethacrylate, polyacrylamide or polymethacrylamide, polyethyleneglycol or polyelectrolytes, can also be used. Polyelectrolytes having acidic or basic side groups can be used in the pH range of aqueous solutions where their solubility is limited. Examples are poly(acrylic and polymethacrylic acids), poly[di(carboxylatophenoxy)phosphazene], sulfonated polymers and copolymers in acidic solutions, poly(vinyl amines), and poly(vinylpyridine) in basic water solutions.

Polymers of any molecular weight can be used in the process that provide a microparticle with the desired properties. A preferred range is 1,000 to 10,000,000 Da.

The period of time of release, and kinetics of release, of the substance from the microparticle will vary depending on the polymer or polymer mixture or blend selected to fabricate the microparticle. Those of ordinary skill in this art will be able to select the appropriate polymer or combination of polymers, and optionally, additives, to achieve a desired effect. In one embodiment, additives such as inorganic salts, BSA (bovine serum albumin), and inert organic compounds are used to alter the profile of substance release.

Release of substrate can be achieved by diffusion or erosion (including degradation) of the polymer matrix, or by a combination of diffusion and erosion. The permeability of polymer, and thus the diffusion rate, can be reduced by introduction or addition of hydrophobic units into the polymer, or by the addition of hydrophobic substances or polymers, such as kaolin, talc, magnesium trisilicate, and polylactide, into the material to be fabricated. The permeability can be increased by the addition of hydrophilic polymers, such as polyethylene glycol, sugar, and poly(vinyl pyrrolidone), or by modifying the polymer with hydrophilic substituents. Erosion of polymer microparticles can be accomplished through the use of biodegradable linkages.

II. Substance to be Incorporated

A wide range of biologically active materials, including biologically-labile materials, can be encapsulated in the polymer at the time of microparticle formation. As used herein, the term biologically labile material refers to a biologically active material that can be adversely affected by harsh conditions, such as heat or organic solvents. The term biologically active material refers to a protein, carbohydrate, nucleic acid, lipid, or a combinations thereof, or an organic molecule including a drug, that causes a biological effect when administered in vivo to an animal, including but not limited to birds and mammals, including humans. Nonlimiting examples are antigens, enzymes, hormones, receptors, peptides, polysaccharides, nucleic acids, nucleosides, nucleotides, liposomes, vitamins, minerals, and viruses. This process can also be used to encapsulate procaryotic and eucaryotic cells, e.g., bacteria, yeast, and mammalian cells, including human cells, and components thereof, such as cell walls, and conjugates of cellular components. A gas, including but not limited to air and carbon dioxide, can also be entrapped in the microparticle to produce a microcapsule for diagnostic imaging. In a preferred embodiment for ultrasound imaging, microparticles are prepared by shear coagulation that contain carbon dioxide.

In one embodiment, an antigen is incorporated into the microparticle. The term antigen includes any chemical structure that stimulates the formation of antibody or elicits a cell-mediated response, including but not limited to protein, polysaccharide, nucleoprotein, lipoprotein, synthetic polypeptide, or a small molecule linked to a protein. The antigen can be administered together with an adjuvant as desired. Examples of suitable adjuvants are the synthetic glycopeptides, muramyl dipeptide and muramyl tripeptide. Other adjuvants include killed *Bordetella pertussis*, the liposaccharide of Gram-negative bacteria, and large polymeric anions such as dextran sulfate. Other adjuvants include, but are not limited to, cytokines, diphtheria toxin, exotoxin A and a mucosal adjuvant such as cholera toxin (ct-A and ct-B). A polymer such as a synthetic polyelectrolyte can also be selected for fabrication of the microparticle that provides adjuvant activity.

Specific antigens that can be loaded into the microparticles described herein include, but are not limited to, attenuated or killed viruses, toxoids, polysaccharides, cell wall and surface or coat proteins of viruses and bacteria. These can also be used in combination with conjugates, adjuvants, or other antigens. For example, Hemophilus influenzae in the form of purified capsular polysaccharide (Hib) can be used alone or as conjugate with diphtheria toxoid. Examples of organisms from which these antigens are derived include poliovirus, rotavirus, hepatitis A, B, and C, influenza, rabies, HIV, measles, mumps, rubella, *Bordetella pertussus, Streptococcus pneumoniae, Diphtheria, Tetanus, Cholera, Salmonella, Neisseria, Shigella,* and *Enterotoxigenic E. coli.*

Microparticles prepared according to this process can also be used to deliver water soluble or water insoluble drugs such as nonsteroidal anti-inflammatory compounds, anesthetics, chemotherapeutic agents, immunosuppressive agents, steroids, antibiotics, antivirals, antifungals, steroidal antiinflammatories, and anticoagulants.

Non-pharmaceutical uses for the microparticles include delivery of food additives, including stabilizers and dispersants or other viscosity modifying agents, controlled and selective delivery of pesticides, herbicides, insecticides, fertilizer, and pheromones, and in color and ink formulations in the printing and ink industry. Fragrances can also be included in the microparticle.

The substances to be incorporated should not chemically interact with the polymer during fabrication, or during the release process.

Polymers loaded as described herein can also be used to coat implantable devices, i.e., stents, catheters, artificial vascular grafts, and pacemakers. The coating can release antibiotics, anti-inflammatories, or anti-clotting agents at a predetermined rate, to prevent complications related to the implanted devices. Controlled delivery devices prepared as described herein can also be used as ocular inserts for extended release of drugs to the eye.

III. Process for the Preparation of Microparticles

The process for the preparation of microparticles described herein includes the steps of: (i) dispersing a substantially water-insoluble (including a hydrophobic or cross-linked hydrophilic) polymer in an aqueous solution in which the substance to be delivered is also dissolved, dispersed or suspended; and then (ii) coagulating the polymer together with the substance by impact forces such as shearing forces in extrusion nozzles, high-speed stirrers, colloid mills, and microfluidizers, to form a microparticle. In an alternative embodiment, the aqueous dispersion of polymer and substance to be delivered is coagulated through the use of electrolytes, pH changes, organic solvents in low concentrations, or temperature changes (including cooling as appropriate).

1. Preparation of Aqueous Dispersion of Hydrophobic Polymer

Polymeric dispersions and their physicochemical specifications are described, for example, in Lehmann, "Chemistry and Application Properties of Polymethacrylate Coating Systems" in "Drugs and The Pharmaceutical Sciences. Vol. 36. Aqueous Polymeric Coatings for Pharmaceutical Dosage Forms" Ed. J. W. McGinity, Marcel Dekker,Inc., New York and Basel, 1989, p. 1–94.

In an aqueous polymeric dispersion, a polymer is dispersed in water or a water-based solution. The Synthetic polymers produced by emulsion polymerization are referred to as synthetic latexes. Product prepared by direct emulsification of already formed polymers in water are referred to as artificial latexes. The terms polymeric dispersions and latexes are often used synonymously.

The particle size is the most important characteristic of a dispersion, and is typically between 10 and 1000 nm. The upper limit, near 1 µm, is imposed by thermal convection and the Brownian movement of the particles. Dispersions which contain significant amounts of particles of a size of 1–3 µm or more in diameter may form sediments after a few hours. Dispersions are characterized by low viscosity even when they a high solid content.

Methods for the preparation of aqueous dispersions of polymers are well known to those of ordinary skill in the art, including by polymer synthesis using emulsion polymerization (synthetic latex) or by dispersing a preformed polymer (artificial latex), described in detail below.

Emulsion Polymerization

Emulsion Polymerization can be accomplished, for example, by emulsifying the desired monomers in water with stirring and adding emulsifiers that stabilize the monomer droplets. The polymerization is started by the addition of initiator, and takes place mainly in the water phase by reaction of dissolved monomer molecules. The molecular weight of the polymer molecules in the latex can be controlled by the concentration and decomposition rate of the initiator. The number of particles per cubic centimeter of the final latex is often between $10^{12}$ and $10^{17}$. The particles often have diameters in the range of 50–200 nm. Synthetic latexes typically have a narrow particle size distribution and good stability. Emulsion polymerization is used for the production of the methacrylic acid copolymers Eudragit L 100-55, L 100, S 100 and the copolymer of the neutral (meth)acrylic esters Eudragit NE 30 D.

Dispersion of a Preformed Polymer

Solid polymer can be dispersed in water as a stable latex. A microfluidizer (M-110, Microfluidics Corporation, Newton, MA), geared colloid mill (e.g. PUC-Vikosator JV 14, Probst & Class Gmbh, Rastatt, Germany) or similar equipment known to those skilled in the art can be used to prepare the dispersion. Hydrophilic methacrylic ester copolymers containing small amounts of quaternary ammonium groups introduced and statistically distributed in the polymer (Eudragit RL 100, RS 100) can be transformed into latex like aqueous dispersions by direct emulsification in hot water (glass vessel equipped with a curved, saber like stirrer, a reflex condenser, and a contact thermometer).

The aqueous mixture from which the dispersion is formed can include an amphophilic polymer or a dispersing agent able to modify the interfacial properties of polymer and stabilize the dispersed particles. Examples of amphophilic polymers are polyvinylpyrrolidone, poly(ethylene oxide-co-propylene oxide). Examples of agents that can modify the interfacial properties of dispersed particles are known, and include but are not limited to sorbitan esters, polysorbates, stearates, polyoxyethylene ethers (e.g. Brij 58 or Triton, sold by Sigma Chemical Company), digitonin, alkyl-glucopyranosides, caprylic acid, cholic acid, taurocholic acid, deoxycholic acid, and the salts of these acids, lauryl sulfate sodium salt, and cetylpyridinium chlorides.

Any amount of polymer can be included in the dispersion that can be coagulated to a desired product. A preferred range of polymer in the dispersion is 20–40% (w/w). In general, the higher the polymer concentration in the dispersion, the higher the encapsulation efficiency. Eudragit NE 30D, for example, is sold in the form of 30 and 40% dispersions. When preparing the dispersion, it should be kept in mind that coagulation of polymeric dispersions can be induced by steep shearing gradients in high-speed stirrers, colloid mills, microfluidizers, electrolytes, pH and temperature changes and organic solvents, and therefore, these factors and components should be avoided during the dispersion preparation.

2. Addition of Substance to the Aqueous Polymeric Dispersion

The substance to be delivered is added to the aqueous polymeric dispersion in any desired concentration that provides the product of interest. In general, approximately between 0.01–90% by weight of substance is combined with the polymer.

The substance can be dissolved in the polymeric dispersion directly or combined with a dispersion in the form of a solution. For example, 1 ml of 10% (w/v) FITC-BSA solution in water can be mixed with 4 ml of EUDRAGIT NE30D to produce a 2% FITC-BSA polymeric dispersion. In a preferred embodiment, the aqueous solution of the substance to be encapsulated is poured into the polymeric dispersion very slowly, and mixed by shaking in a manner that does not cause coagulation at this step.

3. Preparation of Microparticle by Coagulation

Coagulation of polymeric dispersions can be induced by mechanical forces, including steep shearing forces (impact forces), produced in any appropriate manner, including but not limited to by high-speed stirrers, colloid mills, microfluidizers and spray nozzles. In an alternative embodiment and in the appropriate situation, coagulation can be accomplished by the use of electrolytes, pH and temperature changes or organic solvents in low concentrations to yield microparticles of larger size. During coagulation the latex particles are layered together to form solid microparticles containing loose agglomerates of the original latex spheres. In one embodiment, soft polymer are used (i.e., that have a glass transition temperature below the temperature of coagulation) in the coagulation process so that the latex spheres flow together. This process is referred to as coalescence. At this stage the remaining water is forced out of the system, and virtually homogeneous particles of compact polymer are formed. In general, fine particulate dispersions produce better phase formation.

Using a microfluidizer, a polymeric dispersion with the material to be encapsulated is pumped through interaction chambers which have precisely defined microchannels through which jets of liquid pinge or hit against each other. This gives rise to intense turbulence and cavitation, yielding microparticles with a size defined by given thermodynamic conditions. In general, the higher the temperature, the softer the polymer, and the larger the microparticles that can be produced.

As an example, a 7% dispersion of 80% poly(lactic acid)/20% Pluronic™ with a particle size smaller than 10–15 µm can be produced with a M-110 laboratory microfluidizer (Microfluidics Corporation, Newton, MA) under a pressure of 15,000 psi at 0° C. This dispersion can be coagulated into microparticles with a microfluidizer to a size larger than 30–50 µm at 25° C. to incorporate the material codispersed or dissolved.

The simple mixers produce microparticles from the polymeric dispersion by the phenomenon of cavitation and shear. Colloid mills force crude stock through very small clearances (for example, 1/1000 of an inch) between the two opposing phases known as the rotor and the stator, producing particles by shear energy.

The preferred equipment for shear coagulation is a spray nozzle, such as an air-atomizer sold by Turbotak Corporation (Ottawa Canada), or an ultrasonic spray nozzle, such as Sonimist sold by Medsonic, Inc. (Farmingdale, N.Y.).

In one embodiment, a syringe pump is used to pump the polymer dispersion into a spray nozzle equipped with an 18 gauge blunt-end needle. The needle enables the solution to be delivered directly to the point of atomization in the nozzle. The polymer dispersion containing dispersed or dissolved material to be encapsulated is then forced through an orifice in the nozzle under air pressure and sprayed into a water bath. Induced by the steep shearing gradients in the nozzle the latex particles compact into microparticles.

The polymeric dispersion flow rate (syringe pump speed) typically ranges from 100 to 800 µl/min, and is preferably approximately 150 µl/min. In general, the higher the flow rate, the larger the microparticles produced. The air pressure typically ranges from 25 to 75 pounds per square inch, and is preferably approximately 60 pounds per square inch. The distance between the nozzle and the water bath is typically 20 to 45 cm, and preferably approximately 35 cm. Short distances can cause microsphere deformation.

The shape and properties of the microparticles can be manipulated by decreasing the temperature below $T_g$ to prevent coalescence (the temperature can be reduced to −15° C. with salt solutions). If the polymer is bearing charged groups, the permeability and swelling of the particle can be increased or decreased by change in the pH and/or ionic strength of the water bath.

A gas can be encapsulated by the creation of turbulence and cavitation by means of mechanical forces.

IV. Examples of Microparticle Fabrication

Microparticles, and in particular, microspheres, were prepared by the coagulation of an aqueous dispersion of polymer with the entity of interest by shearing forces occurring at an air-atomizing nozzle. Microspheres were dispersed and stabilized in distilled water, however, the pH and ionic strength of water solution can be modified as described above to manipulate the stability, permeability and swelling degree of polymeric matrix as desired.

Using the process described in detail above, one of ordinary skill in the art can produce a wide variety of microparticles with diverse properties. The process described herein is further illustrated in the following non-limiting examples. These examples are merely illustrative, and not intended to limit the scope of the invention.

EXAMPLE 1

Preparation of Microspheres Using Shear Coagulation of Aqueous Dispersion of Neutral Poly(meth)acrylates Microspheres were prepared by spraying 10 ml of a 30% aqueous polymeric dispersion of poly(ethyl acrylate-co-methyl methacrylate) (EUDRAGIT NE 30 D) with molar ratio of 2:1 and mean molecular weight 800,000 Da into a conical flask containing 200 ml of deionized water using a Turbotack air-atomizing nozzle. The dispersion was coagulated by shearing forces occurring inside the nozzle, micronized to 5–15 µm spherical microparticles, collected in water. The flow rate of polymeric dispersion was 150 µm/min and was controlled by a SP200I Syringe pump (World Precision Instruments, U.S.A.). The air pressure was 25 psi, and the distance between the nozzle and the surface of water was 30 cm. Microscopic observations, using phase contrast light microscope (CK2Olimpus Optical Co., LTD, Japan), revealed that resulting microparticles were spherical with average diameter 1–10 µm. Microspheres were concentrated by centrifugation at 2000 for 10 minutes.

EXAMPLE 2

Preparation of Microcapsules Using Shear-coagulation of Aqueous dispersion of Ionic Poly(meth)acrylates Example 1 was repeated using a 30% aqueous dispersion of poly(methacrylic acid-co-ethylacrylate) with a molar ratio of 1:1 and molecular weight of 2500,000 Da (EUDR/ GIT L 30 D). The resulting microspheres were collected in water solution of HCl (pH 4.5). The resulting microparticles were spherical With a diameter of 1–20 microns.

EXAMPLE 3 Formation of Polymeric Microcapsules Incorporating Proteins

EUDRAGIT NE 30 D loaded microspheres were prepared by dissolving 60 mg of fluorescein-labeled bovine serum albumin (FITC-BSA, MW 68,000 Da, sold by Sigma Chemical Company) in 3 ml of 30% aqueous polymeric dispersion, and then spraying the aqueous polymeric dispersion with 2% FITC-BSA into a conical flask containing 200 ml of deionized water using a Turbotack air-atomizing nozzle. The flow rate of the polymeric dispersion was 150 µl/min, the air pressure was 25 psi, and distance between the nozzle and surface of water was 30 cm. Microscopic observation revealed that resulting microparticles were spherical with an average diameter 1–10 µm.

EXAMPLE 4 Polymeric Microparticles Containing Entrapped Protein

The EUDRAGIT NE 30 D microparticles loaded with FITC-BSA (MW 68,000 Da) prepared as described in Example 3 were analyzed to determine the amount of BSA encapsulated in microparticle and thus determine the efficiency of encapsulation. Fluorescence of the microparticles was measured at the excitation/emission wavelength of 485/535 nm (Screen Machine, IDEXX™ PCFIA System) and was also detected in a fluorescent microscope (BH20limpus Optical Co., LTD, Japan). 4.3% w/w BSA relative to dry weight of polymer was recovered, indicating an efficiency of encapsulation of 65%. The release profile of FITC-BSA measured in isotonic solution at 37° C. is illustrated in FIG. 1.

EXAMPLE 5 Effect of Coagulation Conditions on Microsphere Formation

In order to increase the efficiency of FITC-BSA encapsulation, various process conditions, polymeric dispersion flow rates and air pressure were evaluated. All other conditions as set out in Example 5 were kept constant. The highest percent of encapsulation, 65%, was achieved with a flow rate of 150 µl/min, and an air pressure of 25 psi.

EXAMPLE 6 Effect of Protein Loading on Microsphere Formation

In an effort to increase the loading of FITC-BSA in the methods, the process of Example 5 was repeated using 200 mg of FITC-BSA dissolved in a 30% EUDRAGIT NE 30 D dispersion. The loading of FITC-BSA was 4.3% (w/w) relatively to dry polymer weight.

V. Pharmaceutical Administration of Microparticles

The microparticles described herein can be administered to a patient in a variety of ways, including orally, intramuscularly, subcutaneously, by aerosol or other topical application. In a preferred embodiment, the microparticles are applied to a mucosal membrane, such as the lung, nasalphyrngial regions, rectum, or vagina.

The microparticles can be lyophilized and then formulated into an aqueous suspension (preferably 5–45% w/w) prior to use. The microparticles can be resuspended into any appropriate liquid, including but not limited to water, aqueous buffers, aqueous acid or base, or water/alcohol solutions. Alternatively, the microparticles can be formulated into a paste, ointment, cream, or gel.

The microparticle should contain the substance to be delivered in an amount sufficient to deliver to a patient a therapeutically effective amount of compound, without causing serious toxic effects in the patient treated. The desired concentration of active compound in the microparticle will depend on absorption, inactivation, and excretion rates of the drug as well as the delivery rate of the compound from the microparticle. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions. The microparticles can be administered once, or may be divided into a number of smaller doses to be administered at varying intervals of time, depending on the release rate of the particle.

This invention has been described with reference to its preferred embodiments. Variations and modifications of the invention will be obvious to those skilled in the art from the foregoing detailed description of the invention. It is intended that all of these variations and modifications be included within the scope of the appended claims.

We claim:

1. A method for preparing a microparticle, comprising the steps of:
   (i) dispersing a hydrophobic polymer in an aqueous solution in which a substance to be delivered is dissolved, dispersed or suspended; and then
   (ii) coagulating the polymer together with the substance by impact forces.

2. The method of claim 1, wherein the substance is a biologically active material.

3. The method of claim 2, wherein the substance is labile to heat or organic solvents.

4. The method of claim 2, wherein the biologically active material is selected from the group consisting of proteins, carbohydrates, nucleic acids, nucleosides, nucleotides, liposomes, vitamins, drugs and minerals.

5. The method of claim 4, wherein the biologically active material is a polysaccharide.

6. The method of claim 4, wherein the protein is an antigen, enzyme, or hormone.

7. The method of claim 6, wherein the antigen is selected from the group consisting of poliovirus, rotavirus, hepatitis A, B, and C, influenza, rabies, HIV, measles, mumps, rubella.

8. The method of claim 6, wherein the antigen is selected from the group consisting of *Bordetella pertussus,* polysaccarides from *Streptococcus pneumoniae, Diphtheria toxoid, Tetanus toxoid, Cholera, Salmonella, Neisseria, Shigella,* and *Enterotoxigenic E. coli.*

9. The method of claim 4, wherein the drug is selected from the group consisting of nonsteroidal anti-inflammatory compounds, anesthetics, chemotherapeutic agents, immunosuppressive agents, steroids, antibiotics, antivirals, antifungals, steroidal antiinflammatories, and anticoagulants.

10. The method of claim 2, wherein the biologically active material is a procaryotic or eucaryotic cell.

11. The method of claim 10, wherein the cell is selected from the group consisting of bacteria, yeast, and a mammalian cell.

12. The method of claim 2, wherein the biologically active material comprises a component of a cell wall.

13. The method of claim 1, wherein the substance is a gas.

14. The method of claim 1, wherein the hydrophobic polymer is selected from the group consisting of partially or completed esterified polymers or copolymers of acrylic or methacrylic acid, polyphosphazenes, polycarbonates, polylactic acid, polyglycolic acid, copolymers of lactic acid or glycolic acid, polyhydroxybutyric acid, polyorthoesters, polyanhydrides, polysiloxanes, polycaprolactone, and copolymers prepared from the monomers of these polymers.

15. The method of claim 1, wherein the hydrophobic polymer is provided in the form of a copolymer together with monomers of a hydrophilic polymer selected from the group consisting of polyvinylpyrrolidone, polyvinylalcohol, polyhydroxyethylmethacrylate, polyacrylamide, polymethacrylamide, and polyethyleneglycol.

16. The method of claim 1, wherein the impact force is created in an air-atomization nozzle.

17. The method of claim 1, wherein the impact force is created in a pneumatic nozzle.

18. The method of claim 1, wherein the impact force is created in a microfluidizer.

19. The method of claim 1, wherein the impact force is created in a high-speed stirrer or colloid mill.

20. The method of claim 1 wherein the microparticle is spherical.

21. The method of claim 1 wherein the microparticle is irregularly shaped.

22. The method of claim 1, wherein the substance is a fragrance.

23. The method of claim 1, further comprising:
   (iii) dispersing the coagulated polymer in a water solution including an electrolyte.

24. The method of claim 1, further comprising:
   (iii) dispersing the coagulated polymer in a water solution which is adjusted to a preselected pH.

25. The method of claim 1, further comprising:
   (iii) dispersing the coagulated polymer in a water solution which is adjusted to a preselected temperature.

26. The method of claim 25 wherein the water solution is cooled.

* * * * *